United States Patent [19]

Glasow et al.

[11] Patent Number: 4,638,165
[45] Date of Patent: Jan. 20, 1987

[54] DETECTOR APPARATUS AND METHOD FOR COMPUTER TOMOGRAPHY AND RADIOGRAPHY

[75] Inventors: Peter Glasow; Wolfgang Rühle, both of Erlangen, Fed. Rep. of Germany

[73] Assignee: Siemens Aktiengesellschaft, Berlin and Munich, Fed. Rep. of Germany

[21] Appl. No.: 707,352

[22] Filed: Mar. 1, 1985

[30] Foreign Application Priority Data

Mar. 9, 1984 [DE] Fed. Rep. of Germany ....... 3408681

[51] Int. Cl.$^4$ .............................................. G01T 1/22
[52] U.S. Cl. ...................................... 250/370; 357/29
[58] Field of Search .................... 250/370 R, 370 GX; 357/29

[56] References Cited

U.S. PATENT DOCUMENTS 3,974,388 8/1976 Bistler et al. ..................... 250/445 T
4,174,481 11/1979 Leibetruth ....................... 250/445 T
4,292,645 9/1981 Schlosser et al. .......... 250/370 G X

OTHER PUBLICATIONS

IEEE Transactions on Nuclear Science, vol. NS-27, No. 1, 2/80, pp. 252-257.
IEEE Transactions on Nuclear Science, NS-20, No. 1, 2/73, pp. 494-499.
Kaufman et al., "Delay Line Readouts for High Purity Germanium Medical Imaging Cameras," IEEE Trans. on Nuc. Sci., vol. 21, No. 1, pp. 652-657, Feb. 1974.

Primary Examiner—Janice A. Howell
Attorney, Agent, or Firm—Jeffrey P. Morris

[57] ABSTRACT

A detector system for computer tomography or computer radiography contains a plurality of flat detectors which are arranged side by side in the plane of a fan-shaped beam of ionizing rays. According to the invention, detectors of high purity germanium are provided, whose volume is selected so that the contribution of the generation-recombination current to the shot noise of the detectors is substantially smaller than customary in detectors for ionizing rays. With these detectors one obtains a good local resolution as well as a good signal-to-noise ratio and one requires no vacuum and no cooling.

12 Claims, 1 Drawing Figure

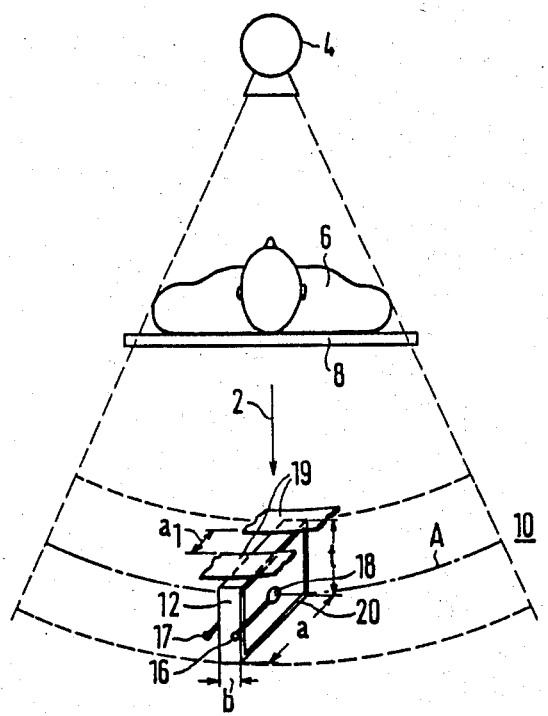

DETECTOR APPARATUS AND METHOD FOR COMPUTER TOMOGRAPHY AND RADIOGRAPHY

BACKGROUND OF THE INVENTION

1. Technical Field

This invention relates to the field of computer tomography and radiography, and more particularly to a detection apparatus and method involving a plurality of flat radiation detectors having an associated semiconductor blocking junction.

2. Description of the Prior Art

Arrangements for making a tomogram are known where a fan-shaped beam of ionizing rays passes through the image elements in the body section plane of a subject to be radiated successively in different directions. Correlated with the beam is a detector arrangement with a plurality of detectors arranged in the body section plane side by side. The conversion of the various single roentgenograms of the body elements and their correlation with the respective image element of the tomogram to be produced are obtained by means of an electronic system which contains a computer. These known arrangements, in which the radiation source with the detector system in the body section plane is rotated about the body step by step, are known in the art as computer tomograms and are disclosed in general and particular detail in U.S. Pat. No. 3,974,388.

Further arrangements for making roentgen shadowgrams of an object, preferably of a human body, are disclosed in U.S. Pat. No. 4,174,481 where, too, a detector system is correlated with a fan-shaped beam of ionizing rays, but where the body is moved relative to the beam after each radiography step by step normal to the fan of the beam. The detectors, therefore, arranged in the radiation plane, successively receive the absorption values of parallel layers of the body. Such arrangements for making roentgen shadowgrams with a movement of the body perpendicular to the fan of the beam are known in the art under the general desgination of computer radiographs.

In computer tomography (CT) and in computer radiography (CR), a detector system with several hundred and often more than one thousand, detectors detects the ionizing radiation, in particular x- or gamma-radiation attenuated by the human body. The particular detector system must document, that is, absorb, the radiation differently attenuated by the individual body parts as completely as possible. Further, the electronic noise of the detector with a particular electronic amplifier type should be small in relation to the quantum noise $\sqrt{N}$ of the minimum roentgen quantum number N occurring during the measuring time, especially at maximum attenuation when the signal to noise ratio is most important. Besides, the detectors should be as fast as possible in a rapid computer tomography apparatus with continuous x-radiation, and, moreover, there should be no afterglow or persistent current which might falsify the x-ray picture.

It is known to use a scintillator-photodiode combination with silicon photodiodes in computer tomography and computer radiography detector systems. Also xenon chambers are sometimes used as detector systems for x-rays. For a high-resolution computer tomography apparatus with continuous x-radiation, however, no known detector fulfills the objectives of the present invention. Cesium iodide, CsI, is generally used in a scintillator-photodiode combination, and while it radiates high signals, it exhibits a disturbing afterglow. Other known scintillators radiate signals smaller by a factor of 4 to 5. Xenon permits only an incomplete absorption of the x-rays. Other problems with xenon are high pressures, high fields at small electrode distance, and problems with a tottering focus of the x-ray tube.

The present detector system for computer tomography contains semiconductor detectors with a flat semiconductor body of n-conducting silicon, whose flat sides are each provided with an electrode, one of which forms a blocking junction designed as a metal-semiconductor junction. One of the end faces of the semiconductor body, about 1.5 mm wide and about 17 mm long, is provided for receiving the radiation. The depth of the semiconductor bodies in the radiation direction is selected to be relatively deep and may be about 20 mm as taught in the publication, "Multichannel Semiconductor Detectors for X-Ray Transmission Computed Tomography," appearing in *IEEE Transactions on Nuclear Science*, Vol. NS-27, No. 1, February, 1980 at pages 252–257. Silicon, however, absorbs only a relatively small portion of the ionizing rays. Even by increasing the depth, for example, to about 40 mm in the direction of the arriving rays, the absorption is not sufficiently complete.

It is further known that detector systems with semiconductor detectors of socalled highest purity or very pure germanium with a very small dopant concentration of, for example, only about $10^{11}$ to $10^9$ atoms/cc are suitable for computer tomography. In a known embodiment of such a detector system, however, operation of the system must be at a cryogenic temperature around 80 K. and in a vacuum because of the narrow band gap of the germanium detectors.

It is also known that nuclear radiation detectors of highest purity germanium of large volume can, in one particular embodiment, indeed be stored at a higher temperature as disclosed in German Pat. No. 25 46 451. However, it has been documented by precise measurements and illustrated by diagrams that germanium detectors can be operated only at temperatures below 150 K. as disclosed in the publication, "Operational Characteristics of Germanium Detectors at Higher Temperatures," appearing in *IEEE Transactions on Nuclear Science*, Vol. NS-20, No. 1, February, 1973 at pages 494–499 (9 D 02).

SUMMARY OF THE INVENTION

The present invention is based on the finding that under specially selected conditions highest purity germanium will meet even the highest requirements of a high-resolution computer tomography apparatus and with continuous x-radiation even at room temperature, but preferably with moderate cooling, for example at 240 K., so that it is not necessary to use a coolant such as liquid nitrogen. The present invention is of the type mentioned above employing detectors having a base material of high-purity germanium but whose volume is selected so that the contribution of the generation-recombination current to the shot noise of the detectors is substantially smaller than the quantum noise of the rays, even at higher temperatures than normal in known detectors of ionizing rays. With this detector system one obtains a good local resolution as well as a good signal-to-noise ratio, and no vacuum is required. Also, for voltageless operation of the detector system, no cooling is required either. In an especially advantageous form of the present detector system, the detectors are provided with a blocking junction made by ion implantation techniques. Thus, not only the generation-recombination current $I_G$, but also the diffusion current $I_D$ remains small, so that also its contribution to the shot noise at higher temperatures remains small. Further, in one prefered embodiment of the detector system, the narrow sides of the detectors are subjected to an after-treatment which limits the surface currents.

The invention is based on the following reasoning. The quantum noise QR of the roentgen quanta has an essential influence on image quality. The mean power of a continuously radiating x-ray tube will generally not substantially exceed 10 kW. At a mean energy of $h\dot{v}=80$ keV, therefore, an average of $N=1.25\times10^5$ quanta/mm$^2$ and ms will arrive at a distance of 1 m. The stochastically independent quanta are subject to Poisson statistics, so that the dispersion is $\sqrt{N}$. An attenuation of the x-rays in computer radiography in the patient by about a factor of 100 and an integration time of 10 ms are normal. Now in a good detector at least 80% of the quanta entering the detector are to be absorbed. We have $N=10^4$ quanta/mm$^2$ for the detector surface and integration time. Thus the quantum noise QR equals $\sqrt{N}=10^2$ and the relative quantum noise thus is 1%. With an inferior detector, which absorbs only about 20% of the quanta, one obtains $N=2.5\times10^3$ quanta/mm$^2$ and QR=50; hence the relative quantum noise QR is 2% and a picture of correspondingly low quality is obtained.

Now it would be possible to select a multiple integration time for poor detectors. Then, however, the dose for the patient would be correspondingly higher and the recording time prolonged; motion blurs would appear. One must, therefore, choose a material for the detector with which as complete as possible an absorption of the roentgen quanta at appropriate absorption depth is obtained.

The absorption of x-rays is known to depend on the nuclear charge number and on the density of the material used. It does not follow a simple exponential law because we are dealing with a continuous ray spectrum, preferably an x-ray spectrum, which is hardened in the detector. The absorption is dependent also on the spectrum before the detector, that is, on the tube voltage, on copper filters, and on whether the spectrum is hardened by the patient. The attenuation of the x-rays occurs not only by photo effect but, in particular for light-weight elements, also by Compton effect. It has now been found that with detectors of highest purity germanium Ge a depth in the direction of the arriving radiation of not substantially more than 8 mm is sufficient for complete absorption.

BRIEF DESCRIPTION OF THE DRAWING

FIG. 1 discloses a schematic drawing of an arrangement for the imaging of parts of a body with a detector system according to the present invention.

DETAILED DESCRIPTION OF THE DRAWING

Referring to FIG. 1, in the illustrated embodiment of apparatus for computer tomography, there is disclosed a fan-shaped beam of ionizing rays 2, preferably gamma-rays, or in particular x-rays, which emanate from a radiation source 4 and pass through an object, such as a part of a human body 6, lying on a plate 8 and a detector system 10 which contains detectors 12 with a base material of highest purity germanium. The detector system 10 may contain preferably several hundred, in particular more than one thousand, of such detectors 12, which are arranged with their flat sides side by side and of which only a single detector 12 is shown for simplification. A part of the upper narrow side of the flat detectors 12, whose flat sides may be rectangular or square is provided for the reception of the rays 2. The detector contains a semiconductor body with a base material of high-purity p-type or n-type germanium, whose concentration of electrically active impurities is less than $10^{13}$ atoms/cc. The carrier life tau$_i$ in the base material is long, for example at least 0.1 ms, preferably at least 1 ms, and if possible, greater than 10 ms. At its two flat sides, having dimensions t by a, the semiconductor body is provided with electrodes which via an electric conductor 16, 17 are connected with an electronic system not shown in FIG. 1. One of the two electrodes forms a blocking junction, which may be preferably a pn junction, and may be produced, for example, by diffusion, in particular, by ion implantation to the surface of the flat side. The blocking junction is produced so that the diffusion current $I_D$ as well as the generation-recombination current $I_G$ remain as small as possible, in order that also the shot noise $\sqrt{i^2}$ of the blocking current $I_S$ will remain minimal.

As a contradoping substance for the production of the pn junction, one may select for p-conducting germanium arsenic As, antimony Sb, or lithium Li, but preferably phosphorus P. A suitable selection for n-conducting germanium is, for example, aluminum Al, gallium Ga, indium In, or beryllium Be, but preferably boron B. For the nonblocking back contact on the opposite flat side, a so-called back surface field contact, with a highly doped layer having a repelling effect for minority charge carriers, there can be implanted in p-conducting germanium, for example, aluminum Al, gallium G, indium In, or beryllium Be, but preferably boron B, and in n-conducting germanium, for example, arsenic As, antimony Sb or lithium Li, but preferably phosphorus P. A metal-semiconductor juncture also may be used for a blocking junction.

For attaching the connecting conductors 16, 17, the electrodes may be provided with a metal contact 18, of which only one is indicated in the FIGURE and which may consist, for example, of palladium, aluminum, gold, or nickel-chromium and may, for example, be vapor-deposited or glued on.

The volume of the semiconductor body is made so small that the shot noise due to the generation-recombination current is substantially less, even at higher temperatures of the detectors 12, than the quantum noise of the rays 2. The width b is essentially determined by the number of detectors 12 and by the width of the fan rays 2. It may be preferably about 0.4 to 1.5 mm, but, in particular, about 0.5 mm. The length a of the detectors 12 is determined by a collimator, not shown, of the radiation source 4, and it may be selected in relatively wide limits of, for example, about 12 to 25 mm, but, in particular, about B 15 mm, for computer tomography, and about 1 to 4 mm, in particular, about 2 to 3 mm, for computer radiography. Associated with the collimator of the radiation source 4 is a device which masks out the effective length a$_1$ of the detectors 12 and which is indicated in the FIGURE as diaphragm 19 with two plates, for simplification. The aperture of the diaphragm 19 and hence the effective length a$_1$ of the detectors 12 may preferably be varied, for example, between about 2 to 12 mm, preferably about 2 to 8 mm for computer tomography and about 1 to 8 mm for computer radiography. The depth t of the detector 12 is chosen so that one obtains an almost complete absorption of the rays 2 in the volume of the detector 12, and it is chosen for computer tomography generally much less than 15 mm, preferably at most 12 mm and in particular less than 10 mm. With a depth t of the base material of the detectors 12 of only 8 mm, about 90% of the rays 2 are absorbed for computer tomography. For computer radiography, a depth t of about 3 to 8 mm, preferably about 4 to 5 mm, is appropriate.

Before installation in the detector system 10, the narrow sides of the detectors 12 can be subjected preferably to a treatment which reduces the surface currents $I_O$ and hence their contribution to the shot noise $\sqrt{i^2}$. For this purpose the narrow sides may be subjected in particular to a re-etching operation, for example, with a mixture of fluoric and nitric acid. In a particular embodiment of the detectors, these re-etched narrow sides are provided with a coating 20 of passivating material, for example, silicon nitride $Si_3N_4$ or silicon dioxide $SiO_2$ or amorphous germanium. Coating 20 may also comprise an adhesive passivating material, in particular, cyanoacrylate.

The detected signal does indeed increase with the number of quanta, and hence with the size of the absorbing volume, and a larger detector thus has a greater response sensitivity, referred to the radiation source. However, also the shot noise of the generation-recombination current $I_G$ increases proportionately with the volume. With the stated small volume, the shot noise remains substantially smaller than the quantum noise and one obtains an absorption of about 90% of the rays.

A blocking current $I_S$ in diodes results in a shot noise $$\sqrt{i^2} = \sqrt{2 e I_s \Delta f},$$

e being the elementary charge of the electron and $\Delta f$ the band width. In the voltageless state, in addition to the blocking current $I_s$, a field current of equal magnitude flows. The variation squares add up, so that one obtains for voltageless operation a total shot noise $$\sqrt{i^2} = \sqrt{4 e I_s \Delta f}$$

Because of its small energy gap, germanium by its nature give high blocking currents at room temperature. These are composed of the generation-recombination current $I_G$ in the entire volume, the diffusion current $I_D$ of the minority charge carriers in the p- and/or n-contact zone, and the surface current $I_O$, and one obtains a total blocking current $$I_S = I_G + I_D + I_O,$$

where $$I_G = \frac{e n_i V}{2 tau_i}$$

and, for example, for an n-contact zone of the semiconductor body $$I_D = e \sqrt{\frac{D_p}{tau_p}} \frac{n_i^2}{N_D} F$$

or accordingly for a p-contact zone $$I_D = e \sqrt{\frac{D_n}{tau_n}} \frac{n_i^2}{N_A} F$$

Here V is the volume of the body, F the surface area of the diode, $D_P$ the diffusion constant of the holes in the n-contact zone, $D_n$ the diffusion constant of the electrons in the p-contact zone, $tau_p$ the life of the holes in the n-contact zone, and $tau_n$ the life of the electrons in the p-contact zone, $N_D$ is the donor concentration in the n-contact zone and $N_A$ the acceptor concentration in the p-contact zone, and $n_i$ the intrinsic conduction concentration of the germanium and $tau_i$ the carrier life in the i-zones. The diffusion current $I_D$ and the surface current $I_O$ can be limited by special preparation. The generation-recombination current $I_G$, however, has a fixed minimum value which is determined by the carrier life $tau_i$ in the base material. The maximum operating temperature of the detectors 12 thus results from a comparison of the generation-recombination current $I_G$ with the quantum noise QR.

In the arrangement shown for computer tomography, with detectors 12 arranged side by side on an arc of a circle for receiving the fan-shaped radiation pattern, the minimum quantum number arriving at the detectors 12 is, for example, $N_{min} = 1.55 \times 10^3$ quanta per 2 ms integration time and 2 mm effective length $a_1$ of the end face, which may preferably be masked out from the length a by means of the diaphragm 19. The mean energy $\overline{E}$ of the spectrum of rays 2 hardened by the body 6 is, for example, 104 ke V and at a depth t of, for example, 8 mm, the detector 12 absorbs about 90% of the rays 2. With an intrinsic conduction concentration of the germanium $n_i = 2.4 \times 10^{13}$ cm$^{-3}$ at room temperature and a carrier life time $tau_i = 10^{-2}$ seconds as well as a band width $\Delta f = 100$ Hz and a pair creation energy $E_i = 3$ eV for detectors 12 with a volume $0.7 \times 13.5 \times 8 = 75.6$ mm$^3$ one obtains a generation-recombination current $I_G = 1.5 \times 10^{-5}$ A and a minimum signal current $i_{min}$ of $3.9 \times 10^{-9}$ A, which result in a shot noise $\sqrt{i^2} = 3.1 \times 10^{-11}$ A and a quantum noise of $1.1 \times 10^{-10}$ A. At room temperature, therefore, the shot noise is only about $\frac{1}{3}$ of the quantum noise. To reduce the blocking current, in particular, the $n_i^2$-proportional current share, it may be desirable to cool the entire detector assembly 10 moderately, preferably to a temperature of about 240 K. and possibly to a temperature of about 200 K.

The setup of the detector system 10 with separate detectors further has the advantage that voltageless operation is possible also at higher temperatures. If the individual detectors form with their associated collimator a separate structure unit, the individual detectors can be replaced without any great expense. Furthermore, by minimizing the radiation distances, unfavorable effects due to focus tottering of the X-ray tube of the radiation source 4 or due to bent collimator plates can be avoided.

In a practical embodiment of the present detector system for computer tomography, the detectors 12 may be arranged side by side preferably in the plane of the fan-shaped beam of rays 2 in approximately equal distance from the radiation source 4 on an arc of circle of the fan of rays 2 so that the flat sides of each of the detectors 12 and of each associated collimator are as parallel as possible to the rays which impinge on the end face of the detector.

A detector system for computer radiography, on the other hand, is generally not curved and the detectors are arranged on a chord of the fan of rays with their flat sides and their associated collimators as parallel as possible to the incident rays.

What is claimed is:

1. A detector system operable without cooling for ionizing rays for computer tomography or computer radiography comprising a plurality of flat detectors which are arranged with their flat sides alongside each other and a narrow side of which is provided for the reception of the ionizing rays, each flat side being provided with an electrode, with one of said electrodes including a blocking junction disposed thereon, the detectors being of high purity germanium and having a particular volume such that the contribution of generation-recombination current to shot noise of the detectors is substantially smaller than the quantum noise of the rays, with the system operating at or below room temperature.

2. A detector system according to claim 1, the blocking junction of each detector junction being produced by ion implantation on its associated flat side.

3. A detector system according to claim 1 or 2, wherein each detector is of a depth measured in the direction of the ionizing rays of less than 15 mm.

4. A detector system according to claim 1, wherein the detectors have a base material with a concentration of electrically active impurities in said base material of less than $10^{12}$ atoms/cc.

5. A detector system according to claim 1, wherein the detector includes a base material of germanium having a concentration of electrically active impurities in said germanium of less than $10^{10}$ atoms/cc.

6. A detector system according to claim 1, wherein the narrow sides of each detector are subjected to a re-etching operation before their installation in the detector system.

7. A detector system according to claim 6, the etched narrow sides of the detectors of which are provided with a coating of a passivating material.

8. A detector system according to claim 7, wherein the passivating coating consists of a cyanoacrylate.

9. A detector system according to claim 1, wherein the detector system is operated at a temperature above 200 K.

10. A detector system according to claim 1, wherein the detector system is operated at a temperature above 240 K.

11. An ionizing radiation detector for computer radiography or computer tomography, the detector comprising a base material of high purity germanium, the detector body being substantially flat and having first and second flat sides and at least one substantially narrow side facing a source of ionizing radiation, each flat side being provided with an electrode, one of said electrodes including a blocking junction disposed thereon with the base material of the flat side of the detector, the volume of the detector body being selected so that the contribution of generation-recombination current to shot noise is much smaller than the quantum noise of the ionizing rays, the detector being operable at room temperature or slightly below.

12. A method of producing an ionizing radiation detector for detection of ionizing radiation from a source of ionizing radiation for computer radiography or computer tomography, the detector of ionizing rays comprising a base material of high purity germanium, the detector body being substantially flat and having first and second flat sides and at least one substantially narrow side facing the source of ionizing radiation, the method comprising the steps of selecting a volume for the detector body such that the contribution of generation-recombination current to shot noise is substantially smaller than the quantum noise of the ionizing rays, fastening a first electrode to the first flat side, producing a blocking junction on the second flat side, fastening a second electrode to the blocking junction, re-etching the narrow sides of the detector, and coating the etched narrow sides of the detector with a passivating coating.

* * * * *